June 2, 1953 E. E. MARSH Plant Pat. 1,191

CLIMBING ROSE PLANT

Filed Feb. 9, 1948

Inventor

EDWARD E. MARSH

By Lyon & Lyon

Attorneys

Patented June 2, 1953

Plant Pat. 1,191

UNITED STATES PATENT OFFICE 1,191

CLIMBING ROSE PLANT

Edward E. Marsh, Pasadena, Calif.

Application February 9, 1948, Serial No. 7,128

1 Claim. (Cl. 47—61)

This invention relates to a new and distinct variety of hybrid tea rose plant originating as a sport on a bush plant of the well known "Faience" rose at my nursery at Pasadena, California. As far as I am able to ascertain, the bush type "Faience" rose is an unpatented variety.

The dominating characteristic of this new rose plant is its strong and vigorous climbing form and its profuse blossoms. There is no apparent tendency to revert to bush form when propagated by budding. In other characteristics, particularly as to form and color, there is no difference notable as it follows very closely the characteristic form of the "Faience" rose of the bush variety.

In the drawings—

Figure 1 is an elevation of climbing rose plant, while

Figure 2:
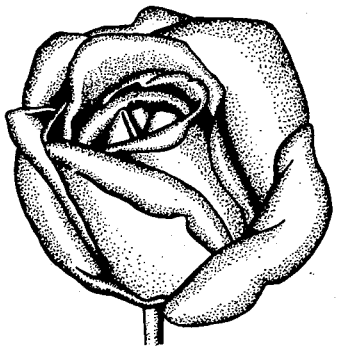
Figure 2 is a reproduction of the rose blossom in partly open condition.
Figure 1:
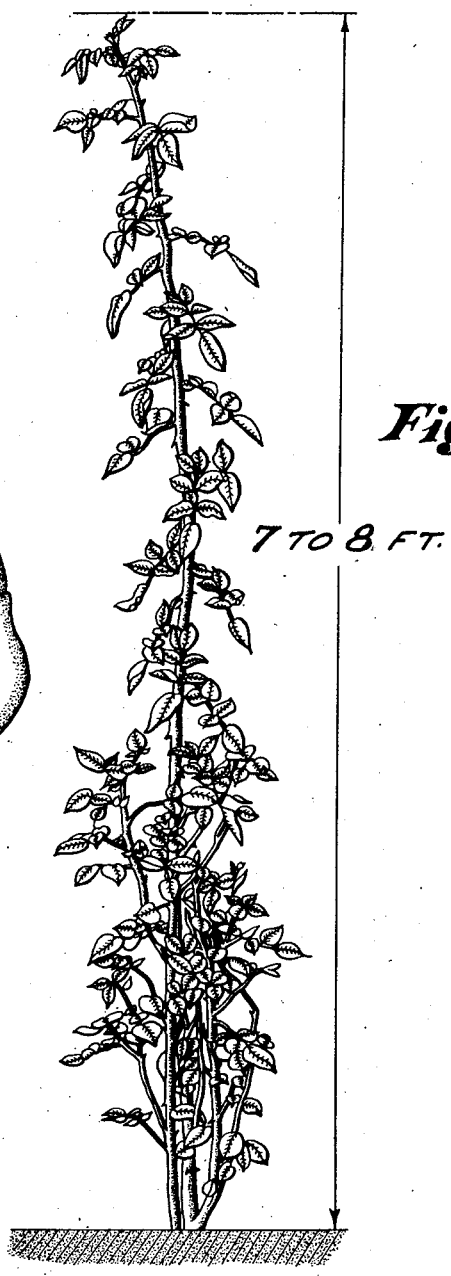

As is true of its parent, the "Faience," the climbing rose plant of this invention produces buds of perfect shape, which gradually open having incurved petals which give the appearance of a cluster of roses.

The color remains bright during the entire blossoming and until the flower drops.

The foliage and wood structure correspond very closely to that of its parent, the "Faience" rose, being in all ways comparable with the plant variety in leaf structure, thorns and other characteristics. In each respect of color, foliage, budding and bloom, the climbing rose plant of this invention truly follows the bush variety of the "Faience" hybrid tea rose.

This sport and its characteristics were observed and its propagation was determined by budding in Altadena, California, where the rose and the climbing rose plant were reproduced by budding and were grown outdoors.

This plant is of the hardy, climbing, outdoor, sport, garden decoration type and is in the hybrid, tea, class.

The flower which is grown in Pasadena, California, and blooms mostly outdoors, bears several flat, normal, long stems. Its continuity is intermittent and it has a moderate tea fragrance.

The bud has a long peduncle of medium weight, which is erect and stiff and is reddish-green in color, with medium texture and numerous red hairs. Before the calyx breaks the size is small. The form is short, pointed, with appendages on the surface of the bud, and with slender foliaceous parts extending beyond the tip of the bud equal to ¼ or more of its length.

As the calyx breaks the color is Chrome Yellow 605/1 to Burnt Orange 014, according to the Horticultural Colour Chart.

As the first petal opens, which it does well, it is of medium size, flat and ovoid. The color outside is Chrome Yellow 605 to 605/1 and inside, Dawn Pink 523 to Mars Orange 013.

The bloom when fully open is of medium size, 4 to 5 inches. The petalage is double, from 45 to 60 petals, and is irregularly arranged. It is flat, cupped at first, becoming open-cupped, the petals remaining at first loosely cupped inward, then later at maturity becoming very loosely rolled outward.

The petals are soft, with satiny inside and satiny outside, and are shaped outside, obovate, with 1 notch; intermediate, obovate and inside, obovate and scalloped. Colors may be modified by being washed.

The following is a description of a newly opened flower from a rose grown outdoors in Pasadena, California, in June 1952:

The color of the outside surface of the outside petal was Chrome Yellow 605 to 605/1; of the inside surface, Dawn Pink 523 to Mars Orange 013; the color of the outside surface of the intermediate petal was Chrome Yellow 605/1 to Mars Orange 013/2; of the inside surface, Vermilion 18/1; the color of the outside surface of the inner petal was Chrome Yellow 605/1 to Mars Orange 013/2; of the inside surface, Vermilion 18.

The following is a description of a rose that was open for three days outdoors in Pasadena, California, in June 1952:

The color of the outside surface of the outside petal was Mimosa Yellow 602/2; of the inside surface, Jasper 018/3; the color of the outside surface of the inside petal was Mimosa Yellow 602/2, of the inside surface, Jasper 018/3 to China Rose 024/2.

The general color effect of the newly opened flower was rosy orange and after open three days it was pink flushed yellow.

The flower blooms unusually well in hot weather and drops off cleanly. Its longevity is 5 days on a bush in a garden in June, and 5 days when kept at living room temperatures in June.

There are several reproductive organs which are: the Stamens, of which there are very many, and which are irregularly arranged; the Filaments, which are medium in size, yellow in color and most are with anthers; the Anthers, which are medium brown in color, and which open at various times; the Pollen, which is very sparse; the Pistils, which are many in number; the Styles, which are even, short, medium texture and very bunched; the Stigma, which is white; the Ovaries, which are all enclosed; the Hips, which are short, flat, ovoid in shape, brown in color, rough in texture and thin; the Sepals, which are permanent, moderately short in length and straight, and the Seeds, which are few in number and medium in size.

The foliage of the plant is as follows:

The leaves, five in a group, are normal, medium in size and moderately thin.

The leaflets are oval shaped, with a mucronate apex, a round base and are simply serrated.

When young the color of the upper surface is moderately red; the under surface, moderately red. When mature, the color of the upper surface is dark green, the under surface, moderately gray green.

The rachis is medium in weight, the upper side is grooved and hairy, and the under side is moderately prickly.

The stipules are of medium length, medium width, with medium points turning out at an angle of more than 45°.

The growth of the plant is moderate, its habit is to climb and it is much branched. The canes are of medium weight. The main stems are dull green in color, with several thorns which are medium in length and straight with broad base, no prickles and no hairs. The branches are dull green in color with several thorns, medium length and straight with broad base, no prickles and no hairs.

All new shoots are dull red in color, with several thorns, medium length and straight with broad base; no prickles and no hairs.

What I claim is:

The new and distinct variety of hybrid tea rose plant as described and illustrated, characterized as to novelty by its strong and vigorous climbing habit and its persistency of reproduction of this characteristic with no apparent tendency to revert to bush form when propagated by budding.

EDWARD E. MARSH.

References Cited in the file of this patent

UNITED STATES PATENTS

| Number | Name | Date |
|---|---|---|
| Pl. Pt. 797 | Marsh | May 4, 1948 |

OTHER REFERENCES

American Rose Annual, vol. 21, page 232 (1936).